US00PP30501P3

(12) United States Plant Patent
Suphachadiwong

(10) Patent No.: US PP30,501 P3
(45) Date of Patent: May 14, 2019

(54) ***VANDA* PLANT NAMED 'SPCDW1609'**

(50) Latin Name: ***Vanda* spp. Jones ex R. Br.**
Varietal Denomination: SPCDW1609

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 0 days.

(21) Appl. No.: 15/932,463

(22) Filed: Mar. 1, 2018

(65) Prior Publication Data

US 2018/0255685 P1 Sep. 6, 2018

(30) Foreign Application Priority Data

Mar. 1, 2017 (QZ) ..... PBR 2017/0652

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ... A01H 5/02; A01H 5/00; A01H 5/08; A01H 6/62
See application file for complete search history.

*Primary Examiner* — June Hwu
(74) *Attorney, Agent, or Firm* — Samuel R. McCoy, Jr.

(57) ABSTRACT

A new and distinct variety of *Vanda* plant named 'SPCDW1609' which is characterized by broad foliage, numerous large flowers borne on a tall inflorescence, flower petals and sepals with a tan base color, petals and sepals which are heavily dotted and blotched with an intense dark purple, a labellum with a dark purple central lobe and yellow lateral lobes which are radially striped dark purple, and the stability of these characteristics from generation to generation.

4 Drawing Sheets

Latin name of the genus and species: The Latin name of the genus and species of the novel variety disclosed herein is *Vanda* spp. Jones ex R. Br.

Variety denomination: The inventive variety of *Vanda* disclosed herein has been given the variety denomination 'SPCDW1609'.

CROSS REFERENCE TO RELATED APPLICATIONS

This application claims priority to the Community Plant Variety Rights application number 2017/0652, filed Mar. 1, 2017, which is herein incorporated by reference.

BACKGROUND OF THE INVENTION

Parentage: The *Vanda* variety 'SPCDW1609' is the result of a planned breeding program. The new variety originated as a seedling from the crossing of *Vanda* 'S34' (not patented), the seed parent, with *Vanda* 'GDBP' (not patented), the pollen parent. Both parents were developed by, and are owned by, the inventor and were never commercially released. The crossing was made by the inventor in his research greenhouse in Bangphra, Thailand in June of 1988.

The new variety was first selected in February of 1993, in a research greenhouse in Bangphra, Thailand belonging to the inventor. After identifying the new variety as a potentially interesting selection, the inventor continued confidential testing and propagation of 'SPCDW1609', assessing stability of the unique characteristics of this variety.

Asexual Reproduction: Asexual reproduction of the new cultivar 'SPCDW1609', by way of mericloning, was first initiated in February of 2005 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1609' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1609'. These characteristics in combination distinguish 'SPCDW1609' as a new and distinct *Vanda* cultivar:

1. *Vanda* 'SPCDW1609' exhibits broad foliage; and
2. *Vanda* 'SPCDW1609' exhibits numerous large flowers borne on a tall inflorescence; and
3. *Vanda* 'SPCDW1609' exhibits lateral petals with a tan base color, moderately suffused with light purple, and dotted and blotched with an intense dark purple color; and
4. *Vanda* 'SPCDW1609' exhibits dorsal sepals with a tan base color, lightly suffused with light purple, and dotted and blotched with an intense dark purple color; and 5. *Vanda* 'SPCDW1609' exhibits lateral sepals with a tan base color, and very heavily blotched with an intense dark purple color which covers most of the sepal surface; and
6. *Vanda* 'SPCDW1609' exhibits a labellum with a dark purple to brown central lobe, and light yellow lateral lobes which are radially striped with dark purple.

BOTANICAL DESCRIPTION OF THE PLANT

Figure 1:
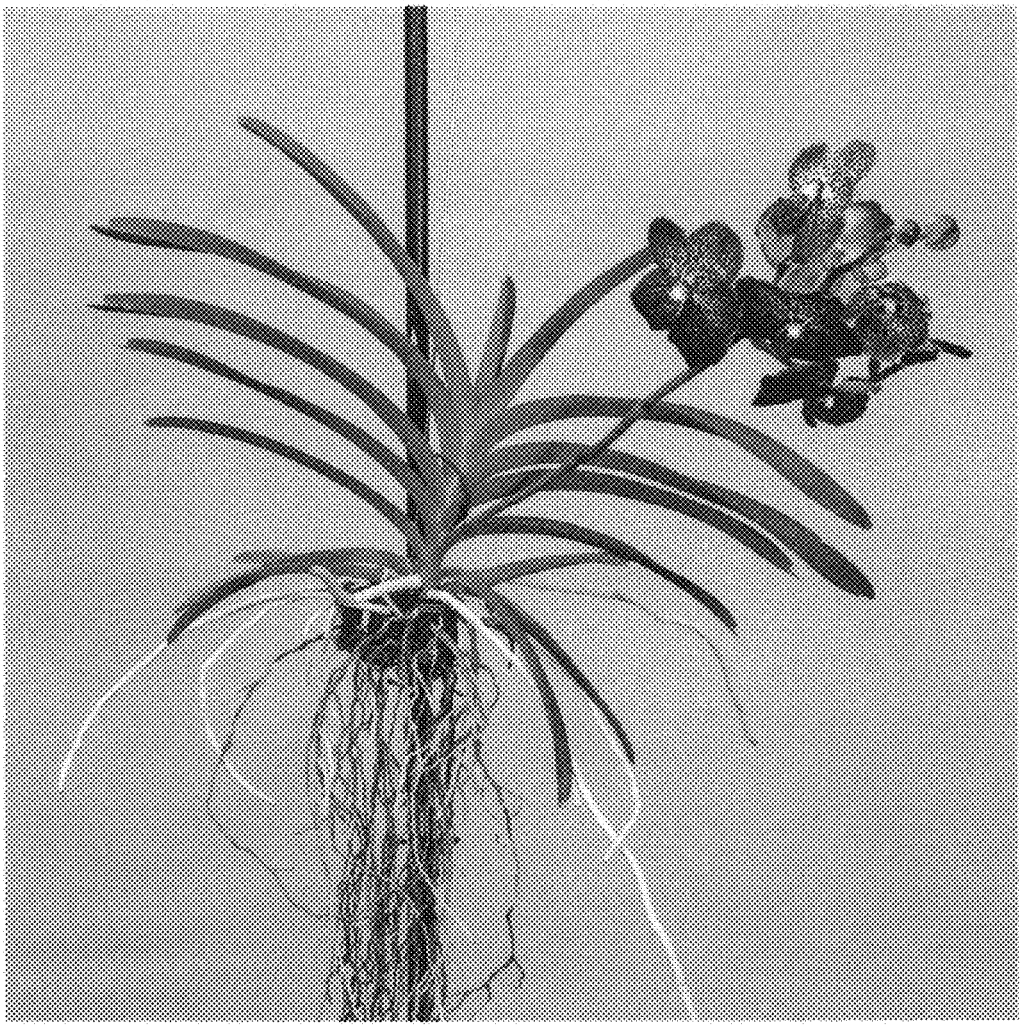
FIG. 1 illustrates, as nearly true as it is reasonably possible to make the same in color photographs of this type, an exemplary plant of 'SPCDW1609' grown in a commercial greenhouse in Honselersdijk, the Netherlands. This plant is approximately 6 years old from the time of meri-cloning, shown planted in an 8 by 2 cm container.
Figure 2:
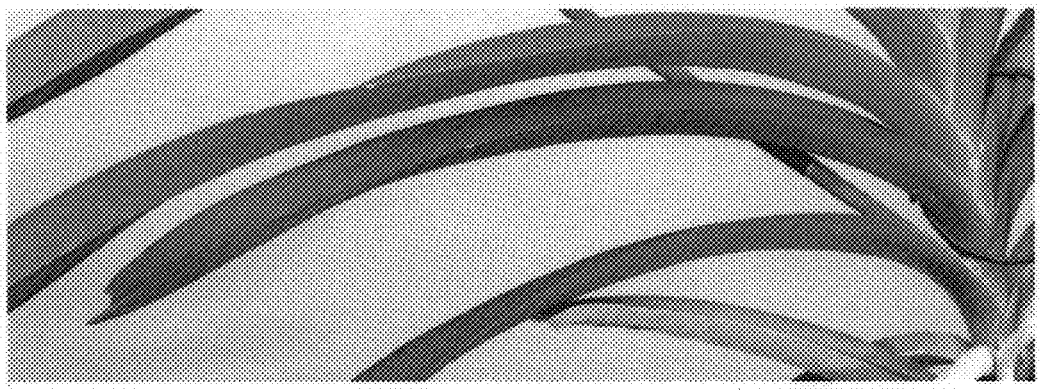
FIG. 2 illustrates, as nearly true as it is reasonably possible to make the same in color photographs of this type, the typical foliage of 'SPCDW1609'.
Figure 3:
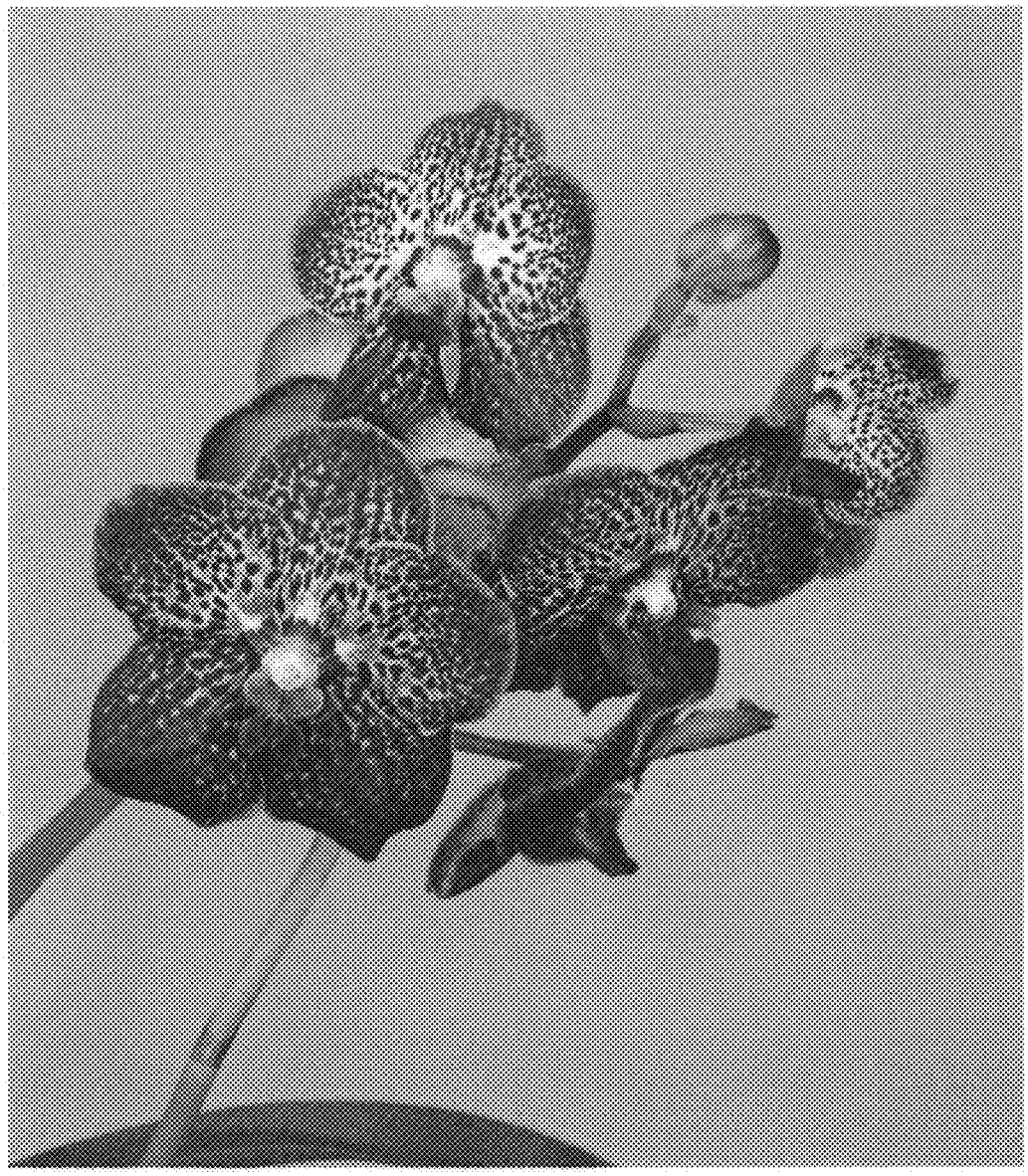
FIG. 3 illustrates, as nearly true as it is reasonably possible to make the same in color photographs of this type, the typical inflorescence of 'SPCDW1609'.
Figure 4:
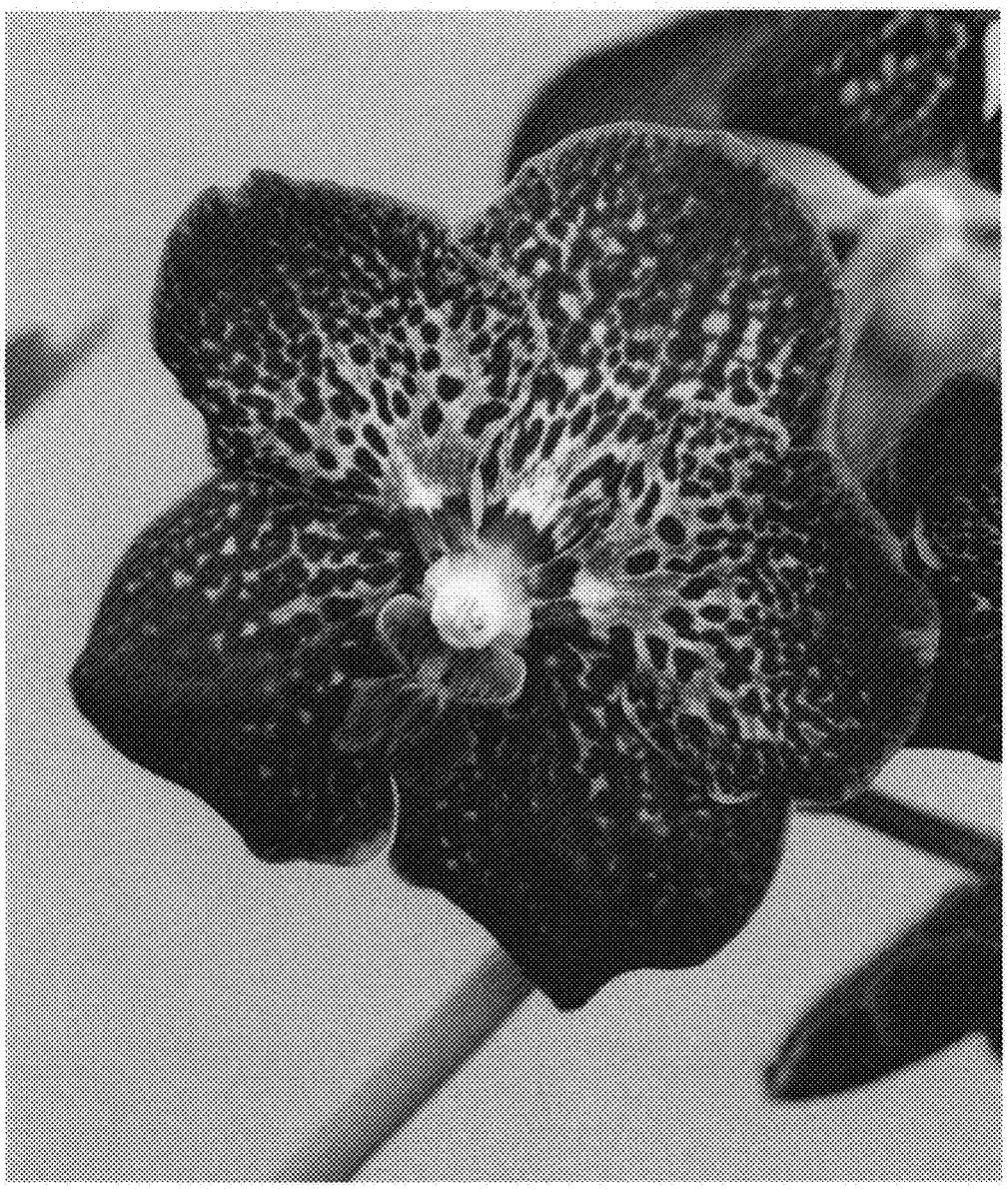
FIG. 4 illustrates, as nearly true as it is reasonably possible to make the same in color photographs of this type, the typical flower of 'SPCDW1609'.

The following observations and measurements made in January of 2018 describe averages from a sample set of six specimens of six year-old 'SPCDW1609' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1609' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart,* The Royal Horticultural Society, London, 2015 (sixth edition).

A botanical description of 'SPCDW1609' and comparisons with the parents and most similar commercial variety of *Vanda* are provided below.

Plant description:

*Growth habit*.—Perennial; monopodial, upright. Single monopodial leafy stem, with flowers carried above the leaf plane; inflorescences growing from the leaf axils.

*Average height from base (plant grown in hanging basket, so no soil line present) to foliar plane*.—28.2 cm.

*Average height from base (plant grown in hanging basket, so no soil line present) to top of floral plane*.—46.5 cm.

*Plant spread*.—Average of 48.2 cm.

*Appropriate container size*.—8 cm by 2 cm rectangular hanging basket.

*Growth rate*.—Moderate.

*Plant vigor*.—Moderate.

*Propagation type*.—Meristematic tissue culture propagation using the base of the leaves.

*Propagation details*.—The time needed from the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.

*Disease and pest resistance or susceptibility*.—Plants have not been observed to be susceptible or resistant to pathogens and pests common to *Vanda*.

*Environmental tolerances*.—Adapt to, at least, USDA Zones 11 and 12 and temperatures as high as 40 degrees Celsius; high tolerance to rain; moderate to high tolerance to wind.

Root system:

*General*.—Moderately dense rooting; with aerial roots only.

*Dimensions, mature roots*.—45.1 cm long with a diameter of 0.6 cm, on average.

*Texture*.—Very fleshy; non-fibrous.

*Color*.—Greyed-green, nearest to RHS 192C; root apex is yellow-green, RHS 148A.

Stem:

*Branching habit*.—Monopodial; no lateral branches present.

*Number of primary (main) stems per plant*.—One.

*Number of secondary (lateral) branches per plant*.—None.

*Appearance and shape*.—Circular, formed by the leaf sheaths.

*Length*.—10.4 cm.

*Diameter*.—1.0 cm.

*Internode length*.—0.9 cm.

*Luster*.—Matte.

*Aspect, main stem*.—Near vertical.

*Strength*.—Very strong.

*Color, juvenile*.—Yellow-green, nearest to RHS 145D.

*Color, mature*.—Green-white, nearest to a combination of RHS 157C and 157D.

*Color at internodes*.—Green-white, nearest to a combination of RHS 157C and 157D.

*Pubescence*.—Glabrous.

Foliage:

*Arrangement*.—Distichous.

*Dimension*.—28.7 cm long, excluding the sheath, and 2.6 cm wide.

*Shape of blade*.—Ligulate; moderately to strongly carinate.

*Aspect*.—Moderately to strongly curved.

*Apex*.—Unequal praemorse.

*Base*.—Sheathing.

*Sheath dimensions*.—4.0 cm long and 1.3 cm wide, on average.

*Sheath color*.—Yellow-green, nearest to in between RHS 145B and 145C.

*Margin*.—Entire.

*Pubescence, texture and luster of adaxial surface*.—Glabrous, smooth, and matte.

*Pubescence, texture and luster of abaxial surface*.—Glabrous, smooth, and matte.

*Color*.—Juvenile foliage, adaxial surface — Green, nearest to RHS 143A, and darker towards the apex and the margins, nearest to RHS 137A. Juvenile foliage, abaxial surface — Green, nearest to RHS 143A, and darker towards the apex and the margins, nearest to RHS 137B. Mature foliage, adaxial surface — Yellow-green, nearest to in between RHS 146A and 147B. Mature foliage, abaxial surface — Yellow-green, nearest to RHS 146B.

*Venation*.—Parallel.

*Venation color, adaxial surface*.—Yellow-green, nearest to in between RHS 146A and 147B.

*Venation color, abaxial surface*.—Green, RHS 143B.

*Petiole*.—No petioles present; leaves sessile.

Inflorescence:

*Inflorescence arrangement*.—Axially placed raceme.

*Natural flowering season*.—Autumn into winter.

*Time to flower*.—Approximately 10 months.

*Flowers per inflorescence*.—Average of 9.

*Flowers per plant*.—8 open flowers and 1 flower buds.

*Inflorescence height*.—Approximately 20.5 cm (measured from base of lowest flower to top of upper flower).

*Inflorescence diameter*.—Approximately 17.8 cm.

*Peduncle*.—Dimensions — Approximately 37.1 cm long and 0.6 cm wide. Aspect — Generally at a 20 degree angle to lateral branch axis. Strength — Moderately strong. Texture and luster — Glabrous and matte. Color — Yellow-green, nearest to a combination of RHS 144A and 144B.

Bud:

*Length*.—Average of 1.6 cm.

*Diameter*.—Average horizontal diameter is 1.8 cm; the vertical diameter is 2.3 cm.

*Shape*.—Cubic, with a deltoid apex which is pointed downward.

*Pubescence, texture and luster*.—Glabrous, smooth and slightly glossy.

*Color*.—Greyed-brown, nearest to RHS 199B, and suffused with greyed-brown at the apex, nearest to a mixture of RHS N199B and 200B; base is yellow-green, nearest to RHS 150B.

Flower:

*Flower type*.—Zygomorphic (orchidaceous), typical shape for the genus *Vanda*.

*Flowering habit*.—Moderately free flowering.

*Shape*.—Zygomorphic, single; consisting of three sepals and three petals, one of which is transformed into a labellum; the two lateral petals moderately overlap the lateral sepals and slightly overlap the dorsal sepal; lateral sepals touching or slightly overlapping one another.

*Attitude*.—Flowers are outward-facing to slightly nodding.

*Vertical height*.—Approximately 9.7 cm.

*Diameter*.—Approximately 9.2 cm.

*Depth*.—Approximately 3.8 cm.

*Fragrance*.—No fragrance.

*Lastingness*.—3 weeks, on average.

*Persistent*.—Self-cleaning.

*Petals*.—Quantity of Petals — Three unfused petals; two conventional petals and one labellum. Arrangement — One lateral petal on each side. Length — Approximately 4.6 cm. Width — Approximately 4.4 cm. Shape — Broad obovate to near orbicular. Apex — Obtuse. Base — Cuneate. Margin — Entire; lightly undulated. Pubescence, texture and luster of upper surface — Glabrous, velvety and matte. Pubescence, texture and luster of lower surface — Glabrous, velvety and matte. Color when opening, upper surface — Green-yellow, nearest to RHS 1C, and fading to greyed-green towards the margins and apex, nearest to RHS 197C; heavily dotted greyed-purple to brown, in between RHS N186C and 200A; base is brown, nearest to RHS 200A. Color when opening, lower surface — Green-yellow, nearest to RHS 1D, and fading to greyed-green towards the margins and apex, nearest to a combination of RHS 197B and 197C; finely dotted greyed-purple at the margins, nearest to RHS N186C. Color when fully opened, upper surface — A mixture of yellow and purple, nearest to RHS 4C and N77B; heavily dotted and blotched greyed-purple, particularly towards the apex, nearest to RHS N186C but darker; base is brown, nearest to RHS 200A. Color when fully opened, lower surface — Greyed-yellow, nearest to RHS 160D, and fading to a mixture of greyed-purple and brown towards the apex, nearest to RHS N187B and N200B; finely dotted greyed-purple at the margins, nearest to RHS N186C. Fading, upper surface — Not fading. Fading, lower surface — Not fading. Venation — Densely reticulate. Venation color, fully opened, upper surface — A mixture of yellow and purple, nearest to RHS 4C and N77B; heavily dotted and blotched greyed-purple, particularly towards the apex, nearest to RHS N186C but darker; base is brown, nearest to RHS 200A. Venation color, fully opened, lower surface — Only the main vein is visible; main vein is yellow, nearest to RHS 13D.

*Labellum*.—Shape — Three-lobed; the shape of the lateral lobes is obovate, and the aspect is involute; the shape of the central lobe is broad oblong, and the aspect is moderately revolute. Length — Central lobe — Approximately 1.9 cm. Lateral lobes — Approximately 1.0 cm. Width — Central lobe — Approximately 1.4 cm; 1.0 at the apex. Lateral lobes — Approximately 0.8 cm. Apex — Central lobe — Emarginate. Lateral lobes — Obtuse. Base — Central lobe — Cuneate. Lateral lobes — Cuneate. Margin — Central lobe — Entire; slightly undulated. Lateral lobes — Entire; not undulate. Texture and luster of upper surface — Central lobe — Glabrous, velvety, and matte. Lateral lobes — Glabrous, velvety, and matte. Texture and luster of lower surface — Central lobe — Glabrous, velvety, and matte with the exception of the apex which is moderately glossy. Lateral lobes — Glabrous, velvety, and matte. Color when opening, upper surface — Central lobe — Purple, nearest to RHS N77A, and fading lighter towards the center, nearest to RHS N77B. Lateral lobes — Yellow, nearest to RHS 8C; radially striped greyed-purple to brown, in between RHS N186C and 200A. Color when opening, lower surface — Central lobe — Greyed-yellow, nearest to a mixture of RHS 160A and 160B; distal one-third portion of the central lobe is purple, in between RHS N77A and N79B. Lateral lobes — Greyed-yellow, nearest to RHS 160C; margined yellow, nearest to RHS 4B; and, radially striped and suffused with purple, nearest to RHS N77A. Color when fully opened, upper surface — Central lobe — A mixture of greyed-purple and brown, nearest to RHS N186C and 200A. Lateral lobes — Yellow, nearest to RHS 8C; radially striped greyed-purple to brown, in between RHS N186C and 200A. Color when fully opened, lower surface — Central lobe — Greyed-green, nearest to RHS 195B; distal one-third portion of the central lobe is greyed-purple to brown, in between RHS N186C and 200A. Lateral lobes — Greyed-yellow, nearest to RHS 160C; radially striped and suffused with greyed-green, nearest to a mixture of RHS 197A and 197B. Fading, upper surface — Not fading. Fading, lower surface — Not fading. Venation — No visible venation. Venation color, fully opened, upper surface — Central lobe — No visible venation. Lateral lobes — No visible venation. Venation color, fully opened, lower surface — Central lobe — No visible venation. Lateral lobes — No visible venation.

*Callosities*.—Dimensions — 1.6 cm long and 0.6 cm wide, on average. Color — In between greyed-purple and brown, nearest to in between RHS N186C and 200A, and fading to yellow towards the base, nearest to RHS 8C.

*Spurs*.—Quantity — Average of 1. Length — Approximately 0.6 cm. Diameter — Approximately 0.25 cm. Vertical height — Approximately 0.6 cm, at the base. Shape — Short triangular; flattened. Apex — Bluntly acute. Base — Broad cuneate. Pubescence, texture and luster — Glabrous, smooth, and matte. Color — Greyed-yellow, nearest to RHS 160C; radially striped and suffused with greyed-green, nearest to a mixture of RHS 197A and 197B.

*Sepals*.—Quantity — Average of 3 unfused sepals. Arrangement — One dorsal sepal and two lateral sepals. Length — Dorsal sepal — Approximately 4.7 cm. Lateral sepals — Approximately 5.0 cm. Width — Dorsal sepal — Approximately 4.7 cm. Lateral sepals — Approximately 5.6 cm. Shape — Dorsal sepal — Near orbicular. Lateral sepals — Reniform. Apex — Dorsal sepal — Obtuse. Lateral sepals — Obtuse. Base — Dorsal sepal — Cuneate. Lateral sepals — Cuneate. Margin — Dorsal sepal — Entire; slightly undulated. Lateral sepals — Entire; highly undulated. Pubescence, texture and luster, upper surface — Dorsal sepal — Glabrous, velvety, and matte. Lateral sepals — Glabrous, velvety, and matte. Pubescence, texture and luster, lower surface — Dorsal sepal — Glabrous, velvety, and matte. Lateral sepals — Glabrous, velvety, and matte. Color when opening, upper surface — Dorsal sepal — Green-yellow, nearest to RHS 1C, and suffused with greyed-green towards the margins and apex, nearest to RHS 197C; base is brown, nearest to RHS 200A; sepal is heavily dotted in between greyed-purple to brown, nearest to in between RHS N186C and 200A. Lateral sepals — Green-yellow, nearest to RHS 154B, and suffused with greyed-green towards the margins and apex, nearest to RHS 197B; base is brown, nearest to RHS 200A; sepal is heavily dotted in between greyed-purple to brown, nearest to in between RHS N186C and 200A. Color when opening, lower surface — Dorsal sepal — Green-yellow, nearest to RHS 1D, and suffused with greyed-green towards the margins and apex, nearest to RHS 197B; central portion is strongly suffused with greyed-green, nearest to RHS 197A; sepal is finely dotted greyed-purple at the margins, nearest to RHS N186C. Lateral sepals — Nearest to in between greyed-yellow and greyed-green, RHS 160B and 195B; suffused with greyed-green towards the margins, nearest to RHS 197B; and, suffused with brown towards the apex, nearest to RHS 200B. Color when fully opened, upper surface — Dorsal sepal — Greyed-yellow, nearest to RHS 160D, and suffused with a mixture of greyed-purple and brown towards the apex, nearest to in between RHS N187B and N200B; finely dotted greyed-purple at the margins, nearest the RHS N186C. Lateral sepals — Green-yellow, nearest to RHS 154B; heavily dotted and blotched with a mixture of greyed-purple to brown, nearest to in between RHS N187B and N200B. Color when fully opened, lower surface — Dorsal sepal — Green-yellow, nearest to a mixture of RHS 1C and 1D, and suffused with purple towards the margins and apex, nearest to RHS N77A; finely dotted greyed-purple at the margins, nearest to RHS N186C. Lateral sepals — Nearest to in between greyed-yellow and greyed-green, RHS 160B and 195B; suffused with greyed-green towards the margins, nearest to RHS 197B; and, suffused with brown towards the apex, nearest to RHS 200B. Fading, upper surface — Not fading. Fading, lower surface — Not fading. Venation — Densely reticulate. Venation color, fully opened, upper surface — Dorsal sepal — Greyed-yellow, nearest to RHS 160D, and suffused with a mixture of greyed-purple and brown towards the apex, nearest to in between RHS N187B and N200B; finely dotted greyed-purple at the margins, nearest the RHS N186C. Lateral sepals — Green-yellow, nearest to RHS 154B; heavily dotted and blotched with a mixture of greyed-purple to brown, nearest to in between RHS N187B and N200B. Venation color, fully opened, lower surface — Dorsal sepal — Only the main vein is visible; main vein is yellow-green, nearest to a mixture of RHS 152C and 152D. Lateral sepals — Only the main vein is visible; main vein is yellow-green, nearest to a mixture of RHS 152C and 152D.

*Pedicels*.—Length — Approximately 6.1 cm. Diameter — Approximately 0.5 cm. Angle — Approximately 80 degree angle to peduncle axis. Strength — Moderate. Texture — Glabrous, axially angled with 5 "ribs", axially twisted (due to resupination). Luster — Glossy. Color — Greyed-purple, nearest to RHS 186D, and fading to greyed-green towards the proximal end, nearest to RHS 197A.

*Bract*.—Quantity — One bract present at the base of each pedicel. Shape — Broad oblong; folded around the base of each pedicel. Dimensions — Average of 1.3 cm long and 1.2 cm wide. Apex — Broad obtuse. Base — Broad cuneate. Margins — Entire. Color, inner surface — Yellow, nearest to RHS 12B, and strongly suffused with brown, RHS 200B. Color, outer surface — Yellow, nearest to RHS 12B, and strongly suffused with brown, RHS 200B.

Reproductive organs:

*Column*.—Length — Approximately 0.7 cm. Diameter — Approximately 0.8 cm. Color — Yellow, nearest to RHS 4D.

*Ovary*.—Position — Inferior. Diameter — Approximately 0.2 cm. Color — Yellow-green, nearest to RHS 150D.

*Pollinia color*.—Yellow-orange, nearest to RHS 17B.

Seed and fruit: No fruit and seed production has been detected to date.

Comparison with the parent plants:

Plants of the new cultivar 'SPCDW1609' differ from the *Vanda* seed parent, 'S34' (not patented), by the characteristics described in Table 1.

TABLE 1

| Characteristic | 'SPCDW1609' | 'S34' |
|---|---|---|
| Height of the inflorescence. | Taller than 'S34'. | Shorter than 'SPCDW1609'. |
| Flower size. | Larger than 'S34'. | Smaller than 'SPCDW1609'. |
| General coloration of the base color on the petals and sepals (excluding the overlain color pattern) when fully opened. | Tan. | Pink. |
| Pattern on the petals and sepals, general coloration. | A mixture of greyed-purple and brown. | Dark pink. |

Plants of the new cultivar 'SPCDW1609' differ from the *Vanda* pollen parent, *Vanda* 'GDBP' (not patented), by the characteristics described in Table 2.

TABLE 2

| Characteristic | 'SPCDW1609' | 'GDBP' |
|---|---|---|
| Plant vigor. | More vigorous. | Less vigorous. |
| Flowering habit. | More freely flowering. | Less freely flowering. |
| Flower size. | Smaller than 'GDBP'. | Larger than 'SPCDW1609'. |

TABLE 2-continued

| | | |
|---|---|---|
| General coloration of the base color on the petals and sepals (excluding the overlain color pattern) when fully opened. | Tan. | Dark violet. |
| Pattern on the petals and sepals, general coloration. | A mixture of greyed-purple and brown. | Blue. |

Comparison with the most similar *Vanda* cultivar known to the inventor:

Plants of the new cultivar 'SPCDW1609' are most similar to the cultivar, *Vanda* 'SPCDW1101' (European Community Plant Variety Rights grant number 33690). A comparison of 'SPCDW1609' with *Vanda* 'SPCDW1101' is described in Table 3.

TABLE 3

| Characteristic | 'SPCDW1609' | 'SPCDW1101' |
|---|---|---|
| Foliage, length. | Shorter than 'SPCDW1101'. | Longer than 'SPCDW1609'. |
| General coloration of the base color on the petals and sepals (excluding the overlain color pattern) when fully opened. | Tan. | Yellow. |
| Pattern on the petals and sepals, general coloration. | A mixture of greyed-purple and brown. | Light purple. |
| Expression of the color pattern on the petals and sepals. | More heavily dotted. | More lightly dotted. |
| Width of the central lobe of the labellum. | Narrower than 'SPCDW1101'. | Wider than 'SPCDW1609'. |

That which is claimed is:

1. A new and distinct variety of *Vanda* plant named 'SPCDW1609', substantially as described and illustrated herein.

* * * * *